(12) United States Patent
Soltis et al.

(10) Patent No.: US 8,996,114 B2
(45) Date of Patent: Mar. 31, 2015

(54) STRAIN RELIEF FEATURE FOR AN IMPLANTABLE MEDICAL DEVICE LEAD

(75) Inventors: Brian D. Soltis, St. Paul, MN (US); Bruce A. Tockman, Scandia, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 3 days.

(21) Appl. No.: 13/532,314

(22) Filed: Jun. 25, 2012

(65) Prior Publication Data

US 2013/0005169 A1    Jan. 3, 2013

Related U.S. Application Data

(60) Provisional application No. 61/502,072, filed on Jun. 28, 2011.

(51) Int. Cl.
*A61N 1/05* (2006.01)

(52) U.S. Cl.
CPC .................................. *A61N 1/0558* (2013.01)
USPC .............................................. 607/37; 607/36

(58) Field of Classification Search
USPC ............................................ 607/36–37, 126
See application file for complete search history.

(56) References Cited

U.S. PATENT DOCUMENTS

| | | |
|---|---|---|
| 4,177,818 A | 12/1979 | De Pedro |
| 4,573,481 A | 3/1986 | Bullara |
| 4,590,946 A | 5/1986 | Loeb |
| 4,590,949 A | 5/1986 | Pohndorf |
| 4,602,624 A | 7/1986 | Naples et al. |
| 4,628,942 A | 12/1986 | Sweeney et al. |
| 4,740,170 A | 4/1988 | Lee et al. |
| 4,920,979 A | 5/1990 | Bullara |
| 4,940,065 A | 7/1990 | Tanagho et al. |
| 4,979,511 A | 12/1990 | Terry, Jr. |
| 5,031,621 A | 7/1991 | Grandjean et al. |
| 5,095,905 A | 3/1992 | Klepinski |
| 5,218,089 A | 6/1993 | Mariotti et al. |
| 5,251,634 A | 10/1993 | Weinberg |
| 5,259,394 A | 11/1993 | Bens |

(Continued)

FOREIGN PATENT DOCUMENTS

| | | |
|---|---|---|
| EP | 0585553 A1 | 6/1993 |
| JP | 2005058456 A | 3/2005 |

(Continued)

OTHER PUBLICATIONS

International Search Report and Written Opinion issued in PCT/US2013/029306, mailed Jul. 18, 2013, 13 pages.

(Continued)

*Primary Examiner* — Christopher D Koharski
*Assistant Examiner* — Michael Carey
(74) *Attorney, Agent, or Firm* — Faegre Baker Daniels LLP (57) ABSTRACT

A lead assembly for an implantable medical device includes a lead body having a proximal end, a distal end, and a longitudinal axis that extends between the proximal end and distal end. The lead assembly also includes a strain relief tube that surrounds a portion of the lead body. The strain relief tube includes a flexible material configured to include contours such that the portion of the lead body surrounded by the strain relief tube maintains a formed shape that varies from the longitudinal axis of the lead body. The contours vary in response to forces on the lead body to prevent strain at the distal end of the lead body.

20 Claims, 3 Drawing Sheets

(56) References Cited

U.S. PATENT DOCUMENTS

| | | | |
|---|---|---|---|
| 5,282,468 A | 2/1994 | Klepinski | |
| 5,324,322 A | 6/1994 | Grill, Jr. et al. | |
| 5,334,438 A | 8/1994 | Saugnac | |
| 5,344,438 A | 9/1994 | Testerman et al. | |
| 5,351,394 A | 10/1994 | Weinberg | |
| 5,358,516 A | 10/1994 | Myers et al. | |
| 5,375,594 A | 12/1994 | Cueva | |
| 5,505,201 A | 4/1996 | Grill et al. | |
| 5,531,778 A | 7/1996 | Maschino et al. | |
| 5,674,272 A | 10/1997 | Bush et al. | |
| 5,689,877 A | 11/1997 | Grill et al. | |
| 5,755,766 A | 5/1998 | Chastain et al. | |
| 5,782,892 A | 7/1998 | Castle et al. | |
| 5,871,530 A | 2/1999 | Williams et al. | |
| 5,913,876 A | 6/1999 | Taylor et al. | |
| 5,964,702 A | 10/1999 | Grill et al. | |
| 6,038,479 A | 3/2000 | Werner et al. | |
| 6,051,017 A | 4/2000 | Loeb et al. | |
| 6,093,197 A | 7/2000 | Bakula et al. | |
| 6,174,329 B1 | 1/2001 | Callol et al. | |
| 6,178,349 B1 | 1/2001 | Kieval | |
| 6,249,708 B1 | 6/2001 | Nelson et al. | |
| 6,292,703 B1 | 9/2001 | Meier et al. | |
| 6,296,659 B1 | 10/2001 | Foerster | |
| 6,308,104 B1 | 10/2001 | Taylor et al. | |
| 6,308,105 B1 | 10/2001 | Duysens et al. | |
| 6,381,499 B1 | 4/2002 | Taylor et al. | |
| 6,423,080 B1 | 7/2002 | Gellman et al. | |
| 6,600,956 B2 | 7/2003 | Maschino et al. | |
| 6,725,096 B2 | 4/2004 | Chinn et al. | |
| 7,047,081 B2 | 5/2006 | Kuzma | |
| 7,054,692 B1 | 5/2006 | Whitehurst et al. | |
| 7,160,298 B2 | 1/2007 | Lawew et al. | |
| 7,212,867 B2 | 5/2007 | Van Venroo et al. | |
| 7,502,650 B2 | 3/2009 | Kieval | |
| 7,536,227 B1 | 5/2009 | Poore et al. | |
| 7,561,923 B2 | 7/2009 | Libbus et al. | |
| 7,711,421 B2 | 5/2010 | Shafer et al. | |
| 7,749,273 B2 | 7/2010 | Cauthen, III et al. | |
| 7,807,925 B2 | 10/2010 | Zarembo | |
| 7,831,311 B2 | 11/2010 | Cross, Jr. et al. | |
| 7,891,085 B1 | 2/2011 | Kuzma et al. | |
| 7,925,352 B2 | 4/2011 | Stack et al. | |
| 7,925,358 B2 | 4/2011 | Beiden et al. | |
| 7,933,662 B2 | 4/2011 | Marshall et al. | |
| 7,957,817 B1 | 6/2011 | Gillespie et al. | |
| 7,974,706 B2 | 7/2011 | Moffitt et al. | |
| 7,996,092 B2 | 8/2011 | Mrva et al. | |
| 8,100,141 B2 | 1/2012 | Slupecki et al. | |
| 8,155,757 B1 | 4/2012 | Neisz et al. | |
| 8,244,372 B1 | 8/2012 | Zhulati et al. | |
| 8,295,948 B2 * | 10/2012 | Barker et al. | 607/132 |
| 8,326,418 B2 | 12/2012 | Sommer et al. | |
| 8,417,343 B2 * | 4/2013 | Bolea et al. | 607/42 |
| 8,452,406 B2 | 5/2013 | Arcot-Krishnamurthy et al. | |
| 8,483,845 B2 * | 7/2013 | Sage | 607/117 |
| 8,548,593 B2 | 10/2013 | Ternes et al. | |
| 8,639,355 B2 | 1/2014 | Soltis | |
| 2002/0116042 A1 | 8/2002 | Boling | |
| 2002/0128700 A1 * | 9/2002 | Cross, Jr. | 607/117 |
| 2003/0040785 A1 | 2/2003 | Maschino et al. | |
| 2003/0236558 A1 | 12/2003 | Whitehurst et al. | |
| 2004/0010303 A1 | 1/2004 | Bolea et al. | |
| 2004/0111139 A1 | 6/2004 | McCreery | |
| 2005/0209655 A1 | 9/2005 | Bradley et al. | |
| 2005/0234512 A1 | 10/2005 | Nakao | |
| 2005/0283246 A1 | 12/2005 | Cauthen, III et al. | |
| 2006/0030919 A1 | 2/2006 | Mrva et al. | |
| 2006/0122675 A1 | 6/2006 | Libbus et al. | |
| 2006/0190042 A1 | 8/2006 | Stone et al. | |
| 2006/0259078 A1 | 11/2006 | Libbus | |
| 2007/0071568 A1 | 3/2007 | Dorstewitz | |
| 2007/0083236 A1 | 4/2007 | Sikora et al. | |
| 2007/0100406 A1 | 5/2007 | Kollatschny et al. | |
| 2007/0118177 A1 | 5/2007 | Libbus et al. | |
| 2007/0142871 A1 | 6/2007 | Libbus et al. | |
| 2007/0173914 A1 | 7/2007 | Kollatschny | |
| 2007/0203556 A1 | 8/2007 | Rutten et al. | |
| 2007/0239243 A1 | 10/2007 | Moffitt et al. | |
| 2007/0255320 A1 | 11/2007 | Inman et al. | |
| 2008/0046058 A1 | 2/2008 | Cross et al. | |
| 2008/0051839 A1 | 2/2008 | Libbus et al. | |
| 2008/0058871 A1 | 3/2008 | Libbus et al. | |
| 2008/0058874 A1 | 3/2008 | Westlund et al. | |
| 2008/0058901 A1 | 3/2008 | Ternes et al. | |
| 2008/0086181 A1 | 4/2008 | Amurthur et al. | |
| 2008/0091255 A1 | 4/2008 | Caparso et al. | |
| 2008/0103407 A1 | 5/2008 | Bolea et al. | |
| 2008/0103545 A1 | 5/2008 | Bolea et al. | |
| 2008/0132987 A1 | 6/2008 | Westlund et al. | |
| 2008/0140092 A1 | 6/2008 | Stone et al. | |
| 2008/0172101 A1 | 7/2008 | Bolea et al. | |
| 2008/0177365 A1 | 7/2008 | Bolea et al. | |
| 2008/0177366 A1 | 7/2008 | Bolea et al. | |
| 2008/0183258 A1 | 7/2008 | Inman | |
| 2008/0195188 A1 | 8/2008 | Libbus et al. | |
| 2008/0234780 A1 | 9/2008 | Smith et al. | |
| 2008/0255613 A1 | 10/2008 | Kaiser et al. | |
| 2009/0048641 A1 | 2/2009 | Libbus | |
| 2009/0210042 A1 | 8/2009 | Kowalczewski | |
| 2009/0259260 A1 | 10/2009 | Bentley et al. | |
| 2009/0275997 A1 | 11/2009 | Faltys et al. | |
| 2009/0276024 A1 | 11/2009 | Bonde et al. | |
| 2009/0318961 A1 | 12/2009 | Stone et al. | |
| 2010/0023088 A1 | 1/2010 | Stack et al. | |
| 2010/0036451 A1 | 2/2010 | Hoffer | |
| 2010/0121405 A1 | 5/2010 | Ternes et al. | |
| 2010/0145221 A1 | 6/2010 | Brunnett et al. | |
| 2010/0168831 A1 | 7/2010 | Korivi et al. | |
| 2010/0211131 A1 | 8/2010 | Williams et al. | |
| 2010/0286553 A1 | 11/2010 | Feler et al. | |
| 2010/0305674 A1 | 12/2010 | Zarembo et al. | |
| 2010/0312320 A1 | 12/2010 | Faltys et al. | |
| 2010/0331938 A1 | 12/2010 | Sommer et al. | |
| 2011/0004281 A1 | 1/2011 | Jones | |
| 2011/0022142 A1 | 1/2011 | Barker et al. | |
| 2011/0040257 A1 | 2/2011 | Behymer et al. | |
| 2011/0060395 A1 | 3/2011 | Cantlon | |
| 2011/0172682 A1 | 7/2011 | Brady et al. | |
| 2011/0172701 A1 | 7/2011 | Wales et al. | |
| 2012/0022617 A1 | 1/2012 | Tockman et al. | |
| 2012/0035691 A1 | 2/2012 | Tockman et al. | |
| 2012/0065702 A1 | 3/2012 | Arcot-Krishnamurthy et al. | |
| 2012/0221087 A1 | 8/2012 | Parnis et al. | |
| 2013/0013045 A1 | 1/2013 | Soltis | |
| 2013/0172973 A1 | 7/2013 | Tockman et al. | |
| 2013/0253615 A1 | 9/2013 | Arcot-Krishnamurthy et al. | |
| 2013/0253624 A1 | 9/2013 | Tockman et al. | |
| 2014/0094888 A1 | 4/2014 | True et al. | |

FOREIGN PATENT DOCUMENTS

| | | |
|---|---|---|
| JP | 2008526299 A | 7/2008 |
| WO | WO9929366 A1 | 6/1999 |
| WO | WO2004052176 A2 | 6/2004 |
| WO | WO2006093685 A1 | 9/2006 |
| WO | WO2007024164 A1 | 1/2007 |
| WO | WO2008088798 A1 | 7/2008 |
| WO | WO2008094349 A1 | 8/2008 |
| WO | WO2009020639 A1 | 2/2009 |
| WO | WO2009025817 A2 | 2/2009 |
| WO | WO2009100242 A2 | 8/2009 |
| WO | WO2011053766 A1 | 5/2011 |
| WO | 2013142053 A1 | 9/2013 |

OTHER PUBLICATIONS

International Search Report and Written Opinion Issued in PCT/US2009/063442, mailed Feb. 1, 2010, 11 pages.

International Search Report and Written Opinion Issued in PCT/US2010/026350, mailed Jun. 2, 2010.

International Search Report and Written Opinion Issued in PCT/US2011/049585, mailed Dec. 19, 2011.

(56) References Cited

OTHER PUBLICATIONS

International Search Report and Written Opinion Issued in PCT/US2012/044020, mailed Sep. 11, 2012, 9 pages.
International Search Report and Written Opinion issued in PCT/US2012/044028, mailed Oct. 1, 2012, 9 pages.
International Search Report and Written Opinion issued in PCT/US2011/020699, mailed Jul. 26, 2011, 24 pages.
International Search Report and Written Opinion issued in PCT/US2012/071812, mailed Sep. 13, 2013, 12 pages.
International Search Report and Written Opinion issued in PCT/US2013/062560, mailed Dec. 17, 2014, 13 pages.
International Search Report and Written Opinion issued in PCT/US2013/062608, mailed Dec. 17, 2014, 13 pages.
Partial International Search Report issued in PCT/US2011/020699, mailed Mar. 24, 2011, 6 pages.
International Search Report and Written Opinion issued in PCT/US2013/077949, mailed Jun. 20, 2014, 15 pages.
International Preliminary Examination Report, Chapter II, issued in PCT/US2013/029306, completed Aug. 19, 2014, 16 pages.
Kirsch, Robert F. et al., "Restoration of Hand and Arm Function by Functional Neuromuscular Stimulation", Period covered: Jun. 1, 2001-Aug. 31, 2006, 71 pages.
Written Opinion of the International Preliminary Examining Authority issued in PCT/US2013/029306, mailed May 8, 2014, 6 pages.
International Search Report and Written Opinion issued in PCT/US2014/015590, mailed May 28, 2014, 14 pages.

\* cited by examiner

STRAIN RELIEF FEATURE FOR AN IMPLANTABLE MEDICAL DEVICE LEAD

CROSS-REFERENCE TO RELATED APPLICATION

This application claims priority to Provisional Patent Application No. 61/502,072, filed Jun. 28, 2011, which is herein incorporated by reference in its entirety.

TECHNICAL FIELD

The present invention relates to medical devices. More specifically, the invention relates to a strain relief feature for a medical device lead body.

BACKGROUND

A significant amount of research has been directed both to the direct and indirect stimulation and sensing of the left and right vagus nerves, the phrenic nerve, the sacral nerve, the cavernous nerve, and portions of the anatomy with baroreceptors (e.g., the carotid artery) to treat a wide variety of medical, psychiatric, and neurological disorders or conditions. For example, stimulation of the vagus nerve has been proposed as a method for treating various heart conditions, including heart failure. The nerves stimulated and/or sensed may be sympathetic or parasympathetic in character.

In a nerve stimulation and sensing system, one or more electrodes are formed on a lead that are electrically connected to an implanted electronic package, such as a pulse generator. Electrical energy is delivered to the electrodes by conductors that extend from the pulse generator at a proximal end of the lead to the electrodes at a distal end of the lead. For direct stimulation of a nerve, the electrodes may be configured to be secured directly to, wrapped around, or laid next to the nerve. The lead should be configured so that the electrodes remain in contact with the nerve to be stimulated.

SUMMARY

Discussed herein are strain relief features that are configured to reduce strain or loading on the distal end of an implantable medical device lead, as well as medical device leads including strain relief features.

In Example 1, a lead assembly for an implantable medical device includes a lead body having a proximal end, a distal end, and a longitudinal axis that extends between the proximal end and distal end. The lead assembly also includes a strain relief tube that surrounds a portion of the lead body. The strain relief tube includes a flexible material configured to include contours such that the portion of the lead body surrounded by the strain relief tube maintains a formed shape that varies from the longitudinal axis of the lead body. The contours vary in response to forces on the lead body to prevent strain at the distal end of the lead body.

In Example 2, the lead assembly according to Example 1, wherein the strain relief tube further comprises one or more suture elements coupled to an exterior of the strain relief tube and configured to secure the strain relief tube to adjacent tissue after shaping the strain relief tube.

In Example 3, the lead assembly according to either Example 1 or 2, wherein the strain relief tube includes preformed contours.

In Example 4, the lead assembly according to any of Examples 1-3, wherein the strain relief tube moves with respect to the lead body.

In Example 5, the lead assembly according to any of Examples 1-4, wherein the strain relief tube is securable to the lead body.

In Example 6, the lead assembly according to any of Examples 1-5, wherein the strain relief tube comprises an embedded mesh material or compression resistant material that facilitates mechanical coupling of the strain relief tube to tissue.

In Example 7, the lead assembly according to any of Examples 1-6, wherein the portion of the lead body surrounded by the strain relief tube is proximate the distal end.

In Example 8, a lead assembly for an implantable medical device includes a lead body having a proximal end, a distal end, and a longitudinal axis that extends between the proximal end and distal end. The lead assembly also includes one or more connectors at the proximal end of the lead body that are each adapted for connection to a pulse generator. The lead assembly further includes one or more electrodes at the distal end of the lead body electrically coupled to the one or more connectors. A strain relief tube surrounds a portion of the lead body. The strain relief tube comprises a flexible material configured to include contours such that the portion of the lead body surrounded by the strain relief tube maintains a shape that varies from the longitudinal axis of the lead body.

In Example 9, the lead assembly according to Example 8, wherein the strain relief tube further comprises one or more suture elements coupled to an exterior of the strain relief tube and configured to secure the strain relief tube to adjacent tissue after shaping the strain relief tube.

In Example 10, the lead assembly according to either Example 8 or 9, wherein the strain relief tube includes preformed contours.

In Example 11, the lead assembly according to any of Examples 8-10, wherein the strain relief tube moves with respect to the lead body.

In Example 12, the lead assembly according to any of Examples 8-11, wherein the strain relief tube is securable to the lead body.

In Example 13, the lead assembly according to any of Examples 8-12, wherein the strain relief tube comprises an embedded mesh material or compression resistant material that facilitates mechanical coupling of the strain relief tube to tissue.

In Example 14, the lead assembly according to any of Examples 8-13, wherein the portion of the lead body surrounded by the strain relief tube is proximate the distal end.

In Example 15, a strain relief element for an implantable medical device lead includes a flexible tube including a lumen configured to receive a portion of a lead body of the implantable medical device lead such that the flexible tube surrounds the portion of the lead body. The flexible tube shapeable to include contours such that the portion of the lead body surrounded by the flexible tube maintains a shape that varies from the longitudinal axis of the lead body.

In Example 16, the strain relief element according to Example 15, and further comprising one or more suture elements coupled to an exterior of the flexible tube and configured to secure the strain relief element to adjacent tissue after shaping the flexible tube.

In Example 17, the strain relief element according to either Example 15 or 16, wherein the flexible tube includes preformed contours.

In Example 18, the strain relief element according to any of Examples 15-17, wherein the strain relief element is securable to the lead body.

In Example 19, the strain relief element according to any of Examples 15-18, and further comprising an embedded mesh material or compression resistant material that facilitates mechanical coupling of the strain relief tube to tissue.

In Example 20, the strain relief element according to any of Examples 15-19, wherein the flexible tube is comprised of a material selected from the group consisting of silicone, polyurethane, polytetrafluoroethylene (PTFE), and polyester.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
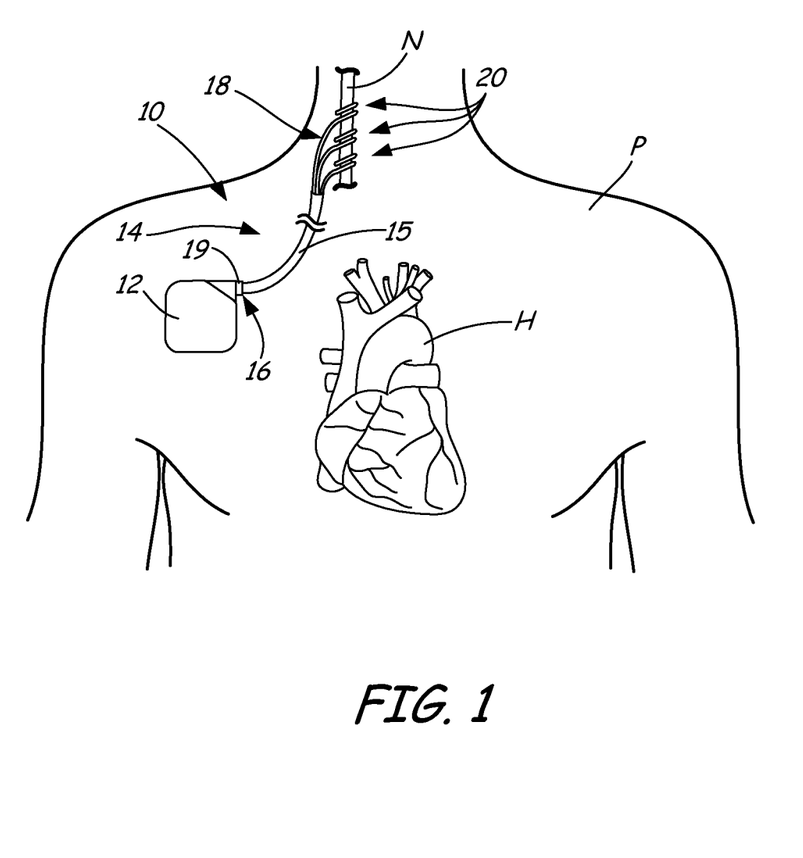
FIG. 1 is an embodiment of a neurostimulation system according to the present invention and portions of an environment in which the neurostimulation system is used.

FIG. 1 shows an embodiment of a neurostimulation system 10 according to the present invention implanted in a patient P. The neurostimulation system 10 includes an implantable medical device (IMD) 12 with a lead 14 including a lead body 15 and having a proximal end 16 and a distal end 18. In one embodiment, the IMD 12 includes a pulse generator. The IMD 12 can be implanted subcutaneously within the body, typically at a location such as in a patient's chest or abdomen, although other implantation locations are possible. The proximal end 16 of the lead 14 can be coupled to the IMD 12 via one or more connectors 19. Alternatively, the lead 14 may be formed integrally with the IMD 12. The distal end 18 of the lead 14, in turn, can be implanted at a desired location in the patient's body to stimulate excitable tissue.

The distal end 18 of the lead 14 includes a plurality of electrode cuffs 20 including one or more rings or spirals containing electrodes. The electrode cuffs 20 are electrically connected to the IMD 12 via one or more conductors (not shown in FIG. 1) extending through the lead 14. The electrode cuffs 20 are formed into a helical shape suitable for coupling to a nerve N, such as a vagus nerve. In some embodiments, at least one of the electrode cuffs 20 may alternatively be configured as an anchor tether or strain relief cuff that secures the electrode assembly to the nerve N.

During operation, the lead 14 delivers electrical signals between the IMD 12 and the electrode cuffs 20. The electrode cuffs 20 may be separately controlled by IMD 12, such that energy having different magnitude, phase, and/or timing characteristics may be delivered to or from each of the electrode cuffs 20. While the lead 14 shown includes three electrode cuffs 20, any number of electrode cuffs having any arrangement on the lead 14 can alternatively be employed in the system 10. In addition, one or more of the electrode cuffs 20 may alternatively be configured as a strain relief cuff that does not carry electrical signals, but secures the distal end 18 relative to the nerve N to minimize movement of the electrode cuffs 20 relative to the excitable tissue due to voluntary or involuntary movements of the patient. Furthermore, the IMD 12 shown is merely by way of illustration, and the IMD 12 may have any configuration suitable for use in conjunction with the lead 14 and may be implanted in any suitable location in the patient's body. For example, the electrode cuffs 20 may alternatively be configured as band electrodes on a straight lead that are placed adjacent to the nerve N to deliver stimulation energy.

The electrode cuffs 20 are configured for stimulation or sensing of a nerve or nerve bundle. In the embodiment shown, the distal end 18 is secured to the vagus nerve N. The electrode cuffs 20 may be arranged around the nerve, with the IMD 12 configured to deliver energy to the electrode cuffs 20 to stimulate the nerve. Stimulating the sympathetic and parasympathetic nervous systems can have effects on physiological parameters associated with the heart H, such as heart rate and blood pressure.

The vagus nerve N has afferent properties, such that the neural stimulation is transmitted to the central nervous system (CNS). Vagal stimulation simultaneously increases parasympathetic and decreases sympathetic activity, and is believed to prevent further remodeling or predisposition to fatal arrhythmias in post-MI patients, to help restore autonomic balance and increase heart rate variability (HRV), to increase parasympathetic and reduce sympathetic tone in hypertrophic cardiac myopathy (HCM), neurogenic hypertension, and arrhythmia protection, to reduce anginal symptoms, to increase coronary blood flow (CBF), and to prevent development or worsening of congestive heart failure (CHF) following MI. The electrode cuffs 20 may be configured and arranged to stimulate the vagus nerve N to provide any of the physiological responses described. While the electrode cuffs 20 are shown arranged around the right vagus nerve N in FIG. 1, the electrode cuffs 20 can be configured and arranged to stimulate the left vagus nerve N to treat other physiological and psychological conditions, such as epilepsy and depression.

After implantation, the lead 14 may become encapsulated with tissue, causing the lead 14 to move in concert with the tissue to which it is attached. For example, when the electrodes 20 are coupled to a vagus nerve, head or torso movement by the patient P may result radial and/or axial force along the lead 14. To reduce strain on the distal end 18 when the patient P moves, the lead body 15 may be formed into or secured in a configuration that allows the lead 14 to extend, flex, or otherwise move while minimizing movement and strain at the distal end 18. For example, the lead body 15 may include one or more bends proximate the distal end 18, which provides additional lead length (i.e., slack) to allow for axial and/or radial movement of the lead 14 when the patient P moves without pulling on the electrode cuffs 20. As another example, the lead body 15 may be arranged to include one or more sinusoidal or waved sections that also reduce movement at the distal end 18 when the patient P moves. As a further example, the lead body 15 may be arranged to include one or more three-dimensional spiral sections. The strain relief assemblies as described herein facilitate forming strain relief shapes or features at any section along the lead body 15 to reduce loading on the distal end 18 of the lead 14.

Figure 2:
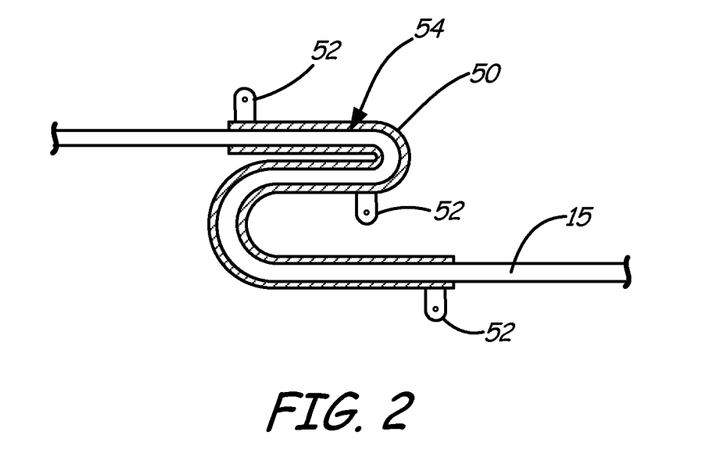
FIG. 2 is a cross-section view of an embodiment of a strain relief tube including suture elements and configured for shaping at implantation.

FIG. 2 is a cross-sectional view of an embodiment of a strain relief tube 50 disposed around the lead body 15 and configured to maintain the lead body 15 in a shape that allows the lead 14 to move with adjacent tissue to minimize load at the distal end 18. The strain relief tube 50 introduces contours in the lead body 15 that vary from the longitudinal axis of the lead 14. The strain relief tube may be include contours that vary in two or three dimensions. The strain relief tube 50 is configured such that, when engaged with the lead 14, surrounds or wraps around the lead body 15. In some embodiments, the strain relief tube 50 may be slid into position over the lead body 15 from the proximal end 16 or distal end 18 of the lead 14. In other embodiments, the strain relief tube 50 includes an opening (e.g., a slit) between its ends to allow strain relief tube 50 to be opened and positioned over the lead body 15 at the desired location.

In some embodiments, the strain relief tube 50 includes one or more suture elements 52 that facilitate securing of the strain relief tube 50 to adjacent tissue. After the strain relief tube 50 is positioned over the lead body 15, the clinician may configure the lead body 15 and strain relief tube 50 into any shape that reduces the load on the distal end 18 during movement of the patient P. This may occur prior to or during implantation of the lead 14. For example, the clinician may secure the electrodes 20 to the nerve N, and subsequently shape the portion of the lead body 15 surrounded by the strain relief tube 50 into the selected configuration. When the lead 14 is positioned and the strain relief tube 50 is shaped, the clinician may secure the strain relief tube 50 to adjacent tissue via the suture elements 52. The strain relief tube 50 may then become encapsulated by the surrounding tissue, allowing the strain relief tube 50 and shaped portion of the lead body 15 to move in concert with surrounding tissue to minimize loading at the distal end 18.

In alternative embodiments, the strain relief tube 50 comprises a pre-shaped or preformed member with the desired shape. The preformed member may be free to move relative to the lead body 14 or may be attached to the lead body 14.

The lead body 15 may be allowed to freely slide within the strain relief tube 50. For example, the diameter of the interior lumen 54 of the strain relief tube 50 may be slightly larger than the outer diameter of the lead body 15 to allow the lead body 15 to move relative to the strain relief tube 50. The strain relief tube 50 may additionally or alternatively be made of a material that reduces friction between the lead body 15 and the strain relief tube 50. In alternative embodiments, the strain relief tube 50 is secured to the lead body 15 to prevent relative movement between the strain relief tube 50 and lead body 15. For example, the strain relief tube 50 may be mechanically or chemically coupled to the lead body 15.

In the embodiment shown, the strain relief tube 50 is arranged in a serpentine configuration including two bends. In this configuration, the lead 14 in the region of the strain relief tube 50 responds to forces in the radial direction with variation in the distance between turns of the strain relief tube 50. The strain relief tube 50 also allows the lead 14 to respond to forces in the axial direction with elongation of the strain relief tube 50 (i.e., unwinding of the turns). The ability of the lead 14 to flex in the region covered by the strain relief tube 50 reduces the amount of load that is transferred to the distal end 18, thereby preventing patient discomfort or migration or dislodgement of the electrodes 20 from the nerve N. The strain relief tube 50 is configured to return to its implanted shape after radial and/or axial forces are no longer applied to the lead 14.

In some embodiments, the strain relief tube 50 is comprised of a flexible biocompatible material. Example materials that are suitable for use in the strain relief tube 50 include, but are not limited to, silicone, polyurethane, polytetrafluoroethylene (PTFE), and polyester. The strain relief tube 50 may also comprise a mesh material to encourage tissue ingrowth and secure the strain relief tube 50 to surrounding tissue. In embodiments in which the strain relief tube 50 is secured to the lead body 15, a mesh component or other compression resistant material may also be embedded into the polymer to facilitate mechanical coupling (e.g., suturing) of the strain relief tube 50 to surrounding tissue.

Figure 3:
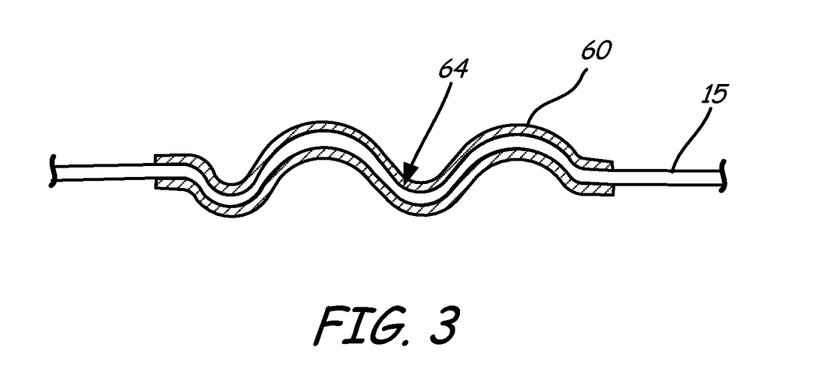
FIG. 3 is a cross-section view of an embodiment of a preformed strain relief tube.

FIG. 3 is a cross-sectional view of an embodiment of a strain relief tube 60 having a preformed shape that reduces loading on the distal end 18 of the lead 14. The strain relief tube 60 surrounds or wraps around the lead body 15 and, after becoming encapsulated with surrounding tissue, moves in concert with the encapsulated tissue. In some embodiments, the strain relief tube 60 may be slid into position over the lead body 15 from the proximal end 16 or distal end 18 of the lead 14. In other embodiments, the strain relief tube 60 includes an opening (e.g., a slit) between its ends to allow strain relief tube 60 to be opened and positioned over the lead body 15 at the desired location. The strain relief tube 60 may be comprised of materials similar to those discussed above with regard to strain relief tube 50.

In the embodiment shown, the strain relief tube 60 is arranged in a waved configuration including multiple undulations. In this configuration, the strain relief tube 60 allows the lead 14 to respond to forces in the axial and/or radial directions with elongation of the strain relief tube 60 (i.e., straightening of the undulations). The strain relief tube 60 is configured to return to its implanted shape after radial and/or axial forces are no longer applied to the lead 14.

The lead body 15 may be allowed to freely slide within the strain relief tube 60. In some embodiments, the diameter of the interior lumen 64 of the strain relief tube 60 may be slightly larger than the outer diameter of the lead body 15 to allow the lead body 15 to move relative to the strain relief tube 60. The strain relief tube 60 may additionally or alternatively be made of a material that reduces friction between the lead body 15 and the strain relief tube 60.

In alternative embodiments, the strain relief tube 60 is secured to the lead body 15 to prevent relative movement between the strain relief tube 60 and lead body 15. For example, the strain relief tube 60 may be mechanically or chemically coupled to the lead body 15. In some embodiments, a mesh component is embedded into the material of the strain relief tube 60 to facilitate mechanical coupling (e.g., suturing) of the strain relief tube 60 and adjacent tissue.

Figure 4:
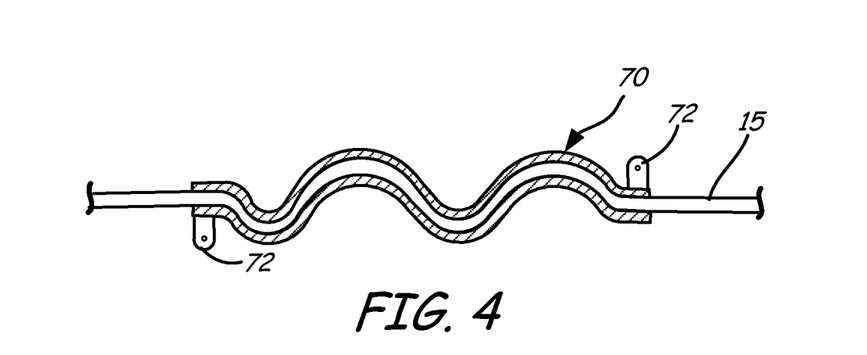
FIG. 4 is a cross-section view of an embodiment of a preformed strain relief tube including suture elements.

FIG. 4 is a cross-sectional view of a strain relief tube 70 having a similar shape and configuration as the strain relief tube 60, and including one or more suture elements 72 that facilitate securing of the strain relief tube 70 to adjacent tissue. After the strain relief tube 70 is positioned over the lead body 15, the clinician may configure the lead body 15 and strain relief tube 70 into any shape that reduces the load on the distal end 18 during movement of the patient P. This may occur prior to or during implantation of the lead 14. For example, the clinician may secure the electrodes 20 to the nerve N, and subsequently shape the portion of the lead body 15 surrounded by the strain relief tube 70 into the selected configuration. When the lead 14 is positioned and the strain relief tube 70 is shaped, the clinician may secure the strain relief tube 70 to adjacent tissue via the suture elements 72. The strain relief tube 70 may then become encapsulated by the surrounding tissue, allowing the strain relief tube 70 and shaped portion of the lead body 15 to move in concert with surrounding tissue to minimize loading at the distal end 18.

Figure 5:
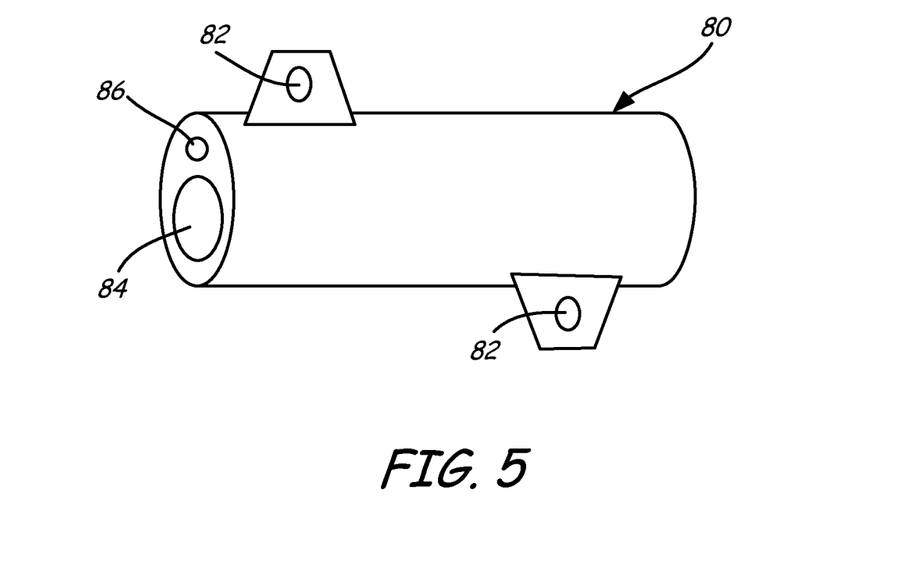
FIG. 5 is a perspective view of an embodiment of a portion of a preformed strain relief tube including a stylet lumen formed in a wall of the strain relief tube.

FIG. 5 is a perspective view of an embodiment of a portion of a strain relief tube 80 having a preformed shape. The strain relief tube 80 may also include one or more suture elements 82 that facilitate securing of the strain relief tube 80 to adjacent tissue. As with earlier described embodiments, the strain relief tube 80 surrounds or wraps around the lead body 15 (not shown) such that the lead body 15 is positioned within lumen 84 After becoming encapsulated with surrounding tissue, moves in concert with the encapsulated tissue. In some embodiments, the strain relief tube 80 may be slid into position over the lead body 15 from the proximal end 16 or distal end 18 of the lead 14. In other embodiments, the strain relief tube 80 includes an opening (e.g., a slit) between its ends to allow strain relief tube 80 to be opened and positioned over the lead body 15 at the desired location. The strain relief tube 60 may be comprised of materials and have characteristics similar to those discussed above with regard to strain relief tubes 50, 60 and 70.

In the embodiment shown in FIG. 5, the strain relief tube 80 also includes a stylet lumen (or straightening wire lumen) 86 configured to receive a stylet or straightening wire during implantation. The lumen 86 may be formed in a wall of the strain relief tube 80. The stylet or straightening wire straightens the preformed shape of the strain relief tube 80 so that the clinician can more easily deliver the lead 14 and coupled strain relief tube 80 to the implant site. The lumen 86 allows for the insertion of a stylet or straightening wire to straighten only the strain relief tube 80 (and portion of the lead 14 therein) such that the entire lead 14 does not straighten during implantation. After positioned at the implant site, the stylet or straightening wire is removed from the lumen 86, and the strain relief tube 80 returns to its preformed shape.

Figure 6:
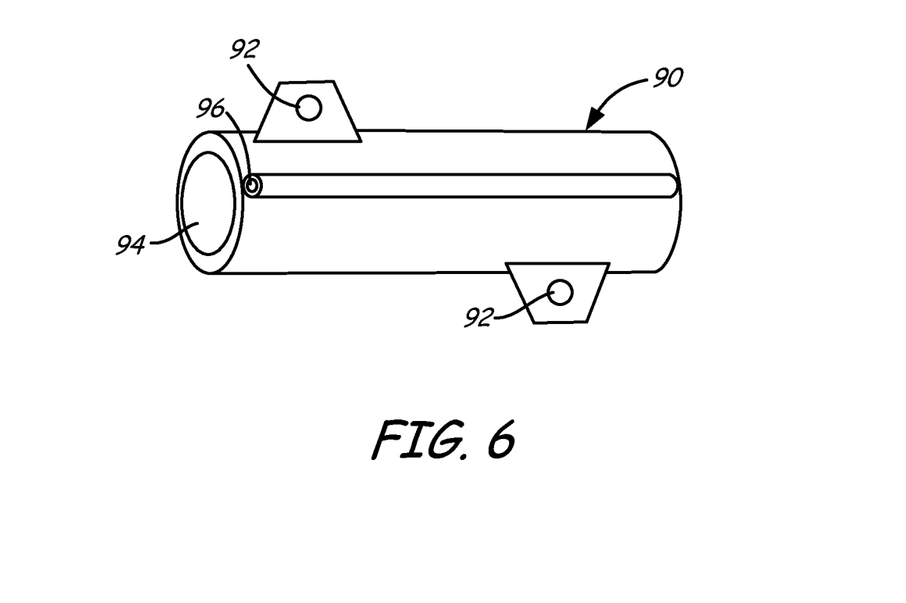
FIG. 6 is a perspective view of an embodiment of a portion of a preformed strain relief tube including a stylet lumen formed on an exterior of the strain relief tube.

The stylet lumen or straightening wire lumen may alternatively have other configurations. For example, FIG. 6 is a perspective view of a portion of a strain relief tube 90 including one or more suture elements 92 that facilitate securing of the strain relief tube 90 to adjacent tissue and a lumen 94 configured to retain a portion of the lead body 15. In this embodiment, a stylet lumen (or straightening wire lumen) 96 is formed on an exterior of the strain relief tube 90. The positioning of the stylet lumen with respect to the strain relief tube may be based on the length and preformed shape of the strain relief tube.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. For example, while the disclosed strain relief assemblies have been described with respect to a neural stimulation system, the disclosed strain relief assemblies may also be employed in association with other types of leads, such as leads in a cardiac stimulation system. Accordingly, the scope of the present invention is intended to embrace all such alternatives, modifications, and variations as fall within the scope of the claims, together with all equivalents thereof.

We claim:

1. A lead assembly for an implantable medical device, the lead assembly comprising:
    a lead body having a proximal end, a distal end, and a longitudinal axis that extends between the proximal end and distal end;
    a stylet, and
    a strain relief tube having an internal lumen and a stylet lumen, the internal lumen sized to receive and surround a portion of the lead body, the strain relief tube formed from a flexible material and having a preformed shape comprising multiple undulations along the length of the strain relief tube such that the portion of the lead body surrounded by the strain relief tube maintains a formed shape that varies from the longitudinal axis of the lead body, the stylet lumen configured to receive the stylet, the stylet configured to straighten the multiple undulations when the stylet lumen receives the stylet, the strain relief tube configured to return to the preformed shape that comprises the multiple undulations upon removal of the stylet from the stylet lumen, wherein the multiple undulations vary in response to forces on the lead body to prevent strain at the distal end of the lead body.

2. The lead assembly of claim 1, wherein the strain relief tube further comprises one or more suture elements coupled to an exterior of the strain relief tube and configured to secure the strain relief tube to adjacent tissue after shaping the strain relief tube.

3. The lead assembly of claim 1, wherein the multiple undulations return to the preformed shape upon removal of the forces.

4. The lead assembly of claim 1, wherein the strain relief tube moves with respect to the lead body.

5. The lead assembly of claim 1, wherein the strain relief tube is securable to the lead body.

6. The lead assembly of claim 5, wherein the strain relief tube comprises an embedded mesh material that facilitates mechanical coupling of the strain relief tube to tissue.

7. The lead assembly of claim 1, wherein the portion of the lead body surrounded by the strain relief tube is proximate the distal end.

8. A strain relief element for an implantable medical device lead, the strain relief element comprising a flexible tube including an internal lumen and a straightening wire lumen, the internal lumen configured to receive a portion of a lead body of the implantable medical device lead such that the flexible tube surrounds the portion of the lead body, the flexible tube having a preformed shape that includes bends along the length of the flexible tubes such that the portion of the lead body surrounded by the flexible tube maintains a shape that varies from the longitudinal axis of the lead body, the bends of the flexible tube configured to straighten when the straightening wire lumen receives a straightening wire, the flexible tube configured to return to the preformed shape that comprises the bend upon removal of the straightening wire from the straightening wire lumen.

9. The strain relief element of claim 8, and further comprising:
    one or more suture elements coupled to an exterior of the flexible tube and configured to secure the strain relief element to adjacent tissue after shaping the flexible tube.

10. The strain relief element of claim 8, wherein the flexible tube is sized to freely slide over the portion of the lead body.

11. The strain relief element of claim 8, wherein the strain relief element is securable to the lead body.

12. The strain relief element of claim 11, and further comprising:
    an embedded mesh material that facilitates mechanical coupling of the strain relief tube to tissue.

13. The strain relief element of claim 8, wherein the flexible tube is comprised of a material selected from the group consisting of silicone, polyurethane, polytetrafluoroethylene (PTFE), and polyester.

14. A lead assembly for an implantable medical device, the lead assembly comprising:
  a lead body having a proximal end, a distal end, and outer diameter, and a longitudinal axis that extends between the proximal end and distal end;
  one or more connectors at the proximal end of the lead body that are each adapted for connection to a pulse generator;
  one or more electrodes at the distal end of the lead body electrically coupled to the one or more connectors; and
  a strain relief tube having an interior lumen configured to receive and surround a portion of the lead body, the strain relief tube formed from a flexible material and having a preformed serpentine shape that includes two bends along the length of the strain relief tube such that the portion of the lead body surrounded by the strain relief tube maintains a shape that varies from the longitudinal axis of the lead body, wherein an inner diameter of the interior lumen is larger than the outer diameter of the lead body such that the strain relief tube freely slides over the lead body when the lead body is received in the interior lumen and the strain relief tube is in the preformed serpentine shape.

15. The lead assembly of claim 14, wherein the strain relief tube further comprises one or more suture elements coupled to an exterior of the strain relief tube and configured to secure the strain relief tube to adjacent tissue after shaping the strain relief tube.

16. The lead assembly of claim 14, wherein the strain relief tube includes contours that vary in three dimensions.

17. The lead assembly of claim 14, wherein the strain relief tube moves with respect to the lead body.

18. The lead assembly of claim 14, wherein the strain relief tube is securable to the lead body.

19. The lead assembly of claim 18, wherein the strain relief tube comprises an embedded mesh material that facilitates mechanical coupling of the strain relief tube to tissue.

20. The lead assembly of claim 14, wherein the portion of the lead body surrounded by the strain relief tube is proximate the distal end.

* * * * *